United States Patent [19]

Freeman

[11] Patent Number: 4,904,391
[45] Date of Patent: Feb. 27, 1990

[54] METHOD AND APPARATUS FOR REMOVAL OF CELLS FROM BONE MARROW

[76] Inventor: Richard B. Freeman, 1920 NW. 31st Ter., Gainesville, Fla. 32605

[21] Appl. No.: 785,729

[22] Filed: Oct. 9, 1985

[51] Int. Cl.⁴ .............................. B03C 1/00; B03C 1/02
[52] U.S. Cl. ...................................... 210/695; 210/222; 210/223; 435/2
[58] Field of Search .................... 210/87, 97, 137, 222, 210/223, 695, 927; 435/2; 424/3, 7.1

[56] References Cited

U.S. PATENT DOCUMENTS 4,508,625  4/1985  Graham .............................. 210/695

FOREIGN PATENT DOCUMENTS

WO85/03649  8/1985  PCT Int'l Appl. ................. 210/695
484894  2/1976  U.S.S.R. ............................ 210/222
1578396  11/1980  United Kingdom ................ 210/222

OTHER PUBLICATIONS

Treleaven et al; "Removal of Neuroblastoma Cells . . . " *The Lancet*, 1/14/84, pp. 70-73.

Primary Examiner—W. Gary Jones
Attorney, Agent, or Firm—Dennis P. Clarke

[57] ABSTRACT

An improved system for removing cells from bone marrow wherein the cells are bound by monoclonal antibodies conjugated to magnetic particles, the system comprising a chamber provided with inlets and outlets for flowing through the chamber a liquid sample containing the bone marrow and magnetic conjugated antibodies bound to the cells and a magnetic field source associated with the chamber wherein the improvement comprises a non-uniform magnetic field in an ascending gradient from the inlet to the outlet.

9 Claims, 3 Drawing Sheets

METHOD AND APPARATUS FOR REMOVAL OF CELLS FROM BONE MARROW

BACKGROUND OF THE INVENTION

1. Field of the Invention

The present invention relates to improvements in systems for removing cells from bone marrow.

2. Prior Art

Monoclonal antibodies bound to e.g., polystyrene microspheres containing magnetite, have been used to remove tumor and other types of cells from bone marrow destined for autologous transplantation. The small magnetic beads can be targeted to the surface of tumor cells to render them magnetic. See Treleaven et al, Lancet, Jan. 14, 1984, pp. 70-73. The flow system which uses permanent samarium cobalt magnets and an electromagnet effects the removal of the "magnetic" tumor cells from the bone marrow. The system is designed to be used with a wide variety of tumor cells, so that by changing panels of monoclonal antibody the system can be used for "cleaning" the bone marrow in many different malignancies.

Although the systems presently in use provide for relatively rapid and efficient removal of the cells, they are subject to several disadvantages. Thus, the general utility of the system is limited by the requirement for a large electromagnet with its associated power supply. Moreover, the system must be assembled only after sterilization of the components. The system is also subject to large variations in the efficiency of conjugated microsphere removal throughout the circuit. There is also no capability for varying the magnetic field strength along the flow path to ameliorate the difficulties associated with the above noted variations along the system. Finally, it is difficult to obtain positive retention of the microspheres on the smooth interior surfaces of the removal chamber.

It is an object of the present invention to provide an improved method and apparatus for the removal of conjugated, magnetic cells from bone marrow which do not suffer from the above noted disadvantages.

SUMMARY OF THE INVENTION

The present invention provides an improvement in a system for removing cells from bone marrow wherein the cells are bound by monoclonal antibodies, conjugated to magnetic particles, the system comprising (1) a chamber provided with inlet and outlet means adapted to enable a flow through the chamber of a liquid sample containing the bone marrow and magnetic conjugated particles bound to the cells and (2) a magnetic field source associated with the chamber such that said liquid sample flowing therethrough passes through the magnetic field whereby only the bound cells are removed from the liquid sample by magnetic attraction, the improvement wherein:

the magnetic field contacting the liquid sample is non-uniform.

The present invention further provides an improvement in a method for removing cells from bone marrow wherein the cells are bound by monoclonal antibodies, conjugated to magnetic particles, the method comprising flowing through a zone provided with an inlet and an outlet a liquid sample containing the bone marrow and magnetic conjugated microspheres bound to the cells, the zone being associated with a magnetic field such that the liquid sample passes through the magnetic field whereby the bound cells are removed from the liquid sample by magnetic attraction, the improvement wherein:

the magnetic field is non-uniform.

DETAILED DESCRIPTION OF THE INVENTION

The system and method of the invention are particularly applicable for the removal of tumor cells, e.g., neuroblastoma cells from bone marrow in chemotherapeutic methods involving autologous bone marrow rescue [See Mal et al, Surg. Gynecol. Obstet., Vol. 150, pp. 193-97 (1980); Blumgart et al, Br. J. Surg. (in press) and Lamois et al, Ann. Surg., Vol. 190, pp. 151-157 (1979)]. Treleaven et al, supra, discloses a system and method for the removal of such malignant cells from bone marrow. The system and method of the present invention are improvements over those disclosed by Treleaven et al, supra.

A critical feature of the present invention resides in the use, as the source of the magnetic field, of an assembly of plural, preferably permanent, magnets arranged in such a manner that the magnetic field contacting the flowing liquid sample is non-uniform.

Most preferably, the magnets are stacked, arranged or magnetically oriented in such a manner that the non-uniform magnetic field is an ascending gradient from the inlet to the outlet of the chamber or zone containing the flowing liquid sample. The gradient is established such that the weakest magnetic attraction is exerted on the sample upon entering the separation chamber and the strongest field is exerted thereon upon exiting the chamber.

This flexibility in being able to create a variable gradient allows the design of a separation protocol which accounts for differences in retained magnetism by the microspheres during manufacture, packed cell volumes and other processing parameters which affect the ability of the microspheres to be attracted by the magnetic field.

The bond between the cell/monoclonal antibody and the magnetic microspheres is relatively weak and subject to disruption by excess jarring, eddy currents or pulsatile flows in the sample, sharp corners in the flow system, etc. It is essential, therefore, that magnetic separation take place in a chamber or zone with smooth walls and no sharp corners and that a steady, even flow of the sample be maintained. Failure to remove all unbound magnetic microspheres from the autologous bone marrow sample may result in microembolisms. Moreover, failure to remove all bound magnetic microspheres would additionally allow tumor cells to be returned to the patient.

A lessened weak magnetic field at the inlet to the separation zone would provide a "soft" attractive force to prevent breaking the bond of the conjugated microspheres at this point on the chamber surface where a large proportion of the bound particles are removed. By increasing the gradient, the magnetic field is intensified as necessary to ensure removal of all of the remaining magnet particles, bound and unbound, prior to exiting the system. Thus, the method and system of the present invention greatly minimizes the chance of disruption of the bound cell/monoclonal antibody and magnetic microspheres conjugate with concomitant re-contamination of the bone marrow with undesired cells as well as ensuring the complete removal of all magnetic particles.

A further preferred feature of the invention is the incorporation in the separation chamber or zone of a mesh element for eliminating movement of the magnetic particles after capture thereof by the magnetic field. A problem associated with the previously used systems is that the smooth surfaces of the chamber walls to which the magnetic microspheres are attracted encourage dislodgement by the flow of the liquid sample, particularly at high flow rates. This is particularly true of the rounded shapes of the conventionally used plastic or resinous microspheres.

The mesh element may be positioned at any location in the chamber which will result in the retention of the magnetic microspheres attracted by the magnetic field. It is preferred to position the mesh element along the full length of the interior wall(s) of the chamber adjacent to the magnetic field, i.e., the wall(s) to which the magnetic particles are attracted. Thus, if a single magnetic field is positioned at one side of the chamber, a single mesh element or layer is positioned along the interior wall of the chamber adjacent to the magnetic field source. If magnetic fields are positioned at more than one wall of the chamber, additional mesh elements or layers are positioned along the interior walls of the chamber adjacent each magnetic field.

A further preferred feature of the invention comprises the inclusion in the system of means for monitoring the flow of the liquid sample through the chamber.

A still further preferred feature of the invention is the provision in the system of means for controlling the flow of liquid sample through the chamber in response to signals from the flow monitoring means to ensure a steady, even, non-bond disruption flow of the sample through the system.

The invention is further illustrated by the accompanying drawings wherein.

DETAILED DESCRIPTION OF THE DRAWINGS

Figure 1:
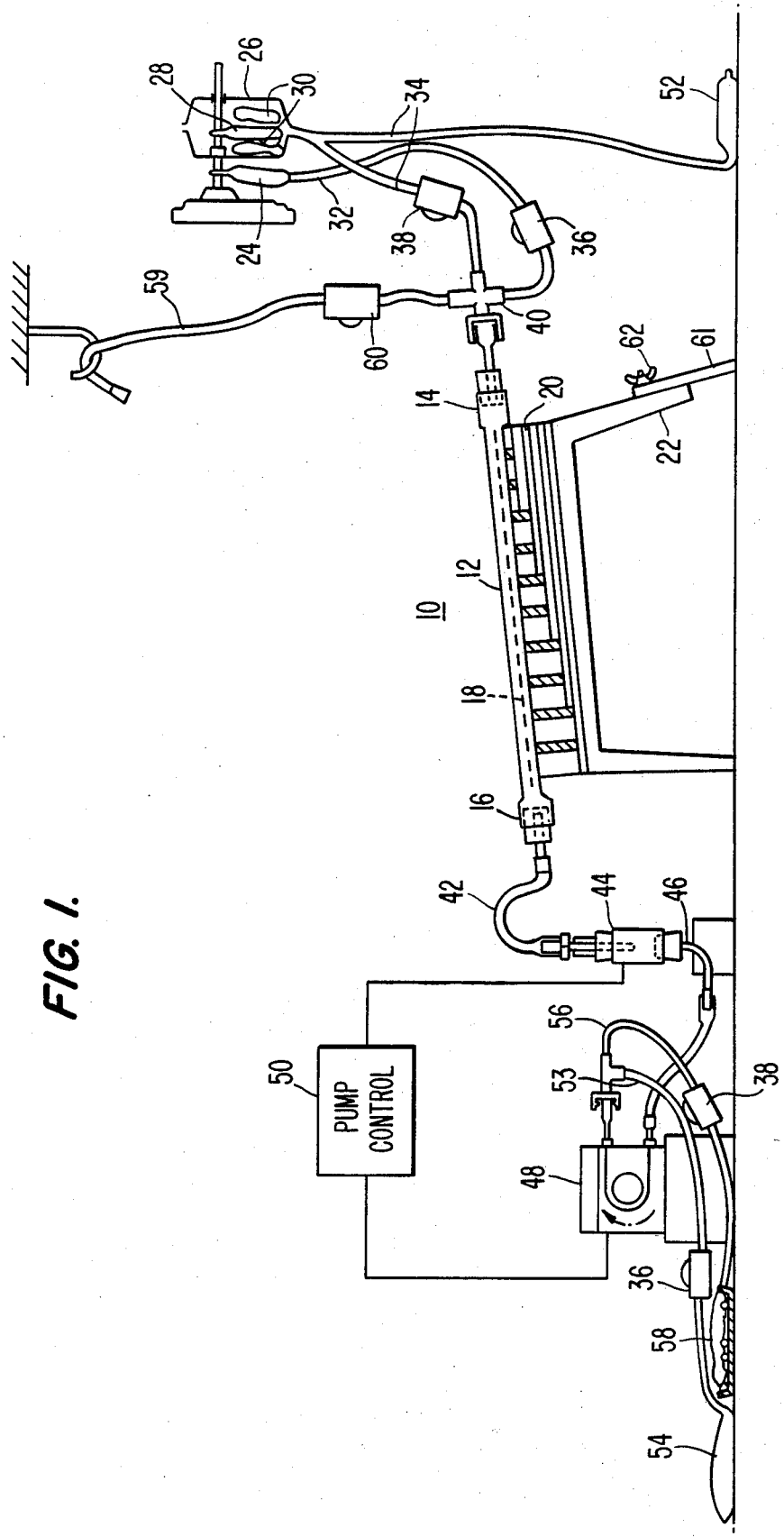
FIG. 1 is a side elevational view of the system of the invention.

Referring to FIG. 1, the cell separation system 10 consists of the separation or perfusion chamber 12, preferably constructed of polycarbonate or other non-toxic sterilizable material to ensure a smooth flow of liquid therethrough. The chamber may be of any desired shape but is preferably substantially cylindrical at the inlet and outlet and uniform in cross-section except for an exterior flat wall surface(s) for placement upon the magnet assembly comprising plural magnets.

The chamber is provided with inlet 14 and outlet 16 means, respectively, for the flow of bone marrow-containing liquid sample. The chamber is provided with mesh element 18 positioned along the lower wall thereof adjacent to the magnet assembly 20 which is conveniently located on table 22.

The liquid sample is provided by a supply system comprising a saline supply 24 and a bone marrow supply. The latter preferably consists of container 26 which houses a source of bone marrow 28 surrounded by ice packs 30 or other temperature maintaining means to keep the marrow cold. Saline and bone marrow are conveyed through lines 32 and 34, respectively, to the inlet 14 of the chamber 12. Flow of the saline and bone marrow is controlled by valves 16 and 38, respectively, and the flow of saline and bone marrow may be combined at +-connector 40 prior to entry into the chamber 12.

Upon flowing through the chamber 12 the magnetic microsphere cell conjugates and microspheres are deflected by the magnet assembly 20 and collect on the mesh 18 to form an amorphous sediment which is firmly anchored by the mesh.

The liquid sample continues flowing through outlet 16 into line 42 where it is conveyed through flow meter 44 which monitors the rate of flow.

The liquid sample then flows through line 46 and into pump 48 [which may be peristaltic, gravity or chamber type] which operates to propel the fluid sample throughout the entire system either in response to signals from the flow monitoring device 50 conveyed by sensing and control system or at a pre-set rate of flow determined by circuit parameters and other physiological criteria. The product sample is conveyed through line 56 to container 58.

The saline supply may be used to prime the cell separation system including the pump and flow meter prior to perfusion. In operation, flow control valves 36 and 38 are shut off and the marrow supply source 28 lowered to position 52. The supply valves 36 and 38 are slowly opened to fill the lines with saline and eliminate air. The valve 38 on the marrow supply line 34 is closed and the saline supply valves 36 are opened and the system primed with saline. When the system is completely filled (saline is ultimately delivered through the system and from pump 48 via line 53 to container 54) and all air pockets eliminated, the system is ready for perfusion.

Adjusting leg 61 by means of clamp element 62 permits elevation of the inlet end of chamber 12 to enhance recovery of viable cells which may otherwise be prone to remain on the horizontal surfaces of the chamber.

After perfusion, any viable cells remaining in the chamber may be flushed with saline as described above for priming, or flow control valve 60 on line 59 may be opened and any viable cells remaining in the chamber 12 will be emptied into the marrow collection pack without the addition of flushing saline (air flushing).

Figure 2:
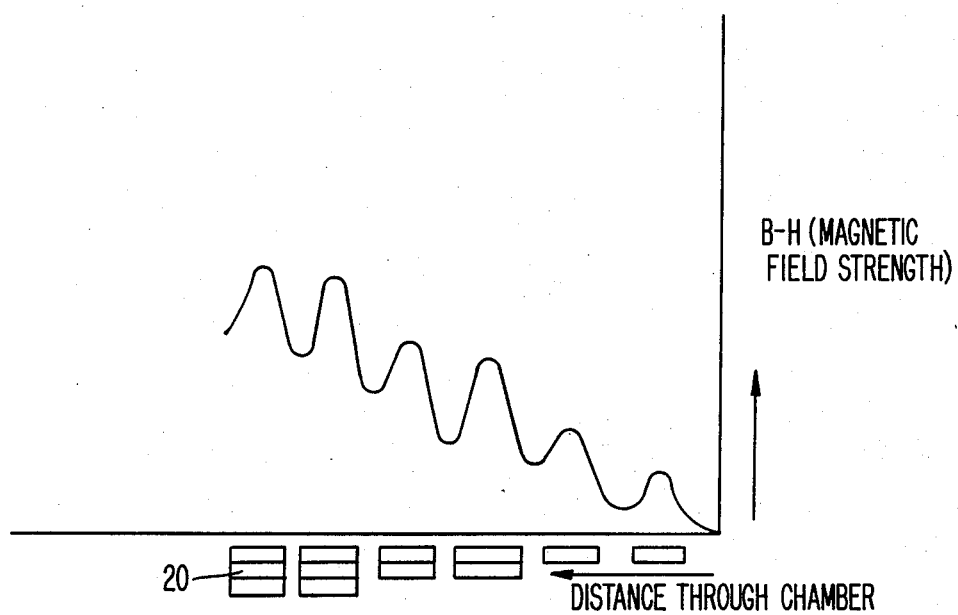
FIG. 2 is a depiction of the intensity of the magnetic field across the separation chamber.

FIG. 2 depicts the ascending gradient magnetic field generated from the inlet to the outlet of the chamber by the multiple stacked magnets.

Figure 3:
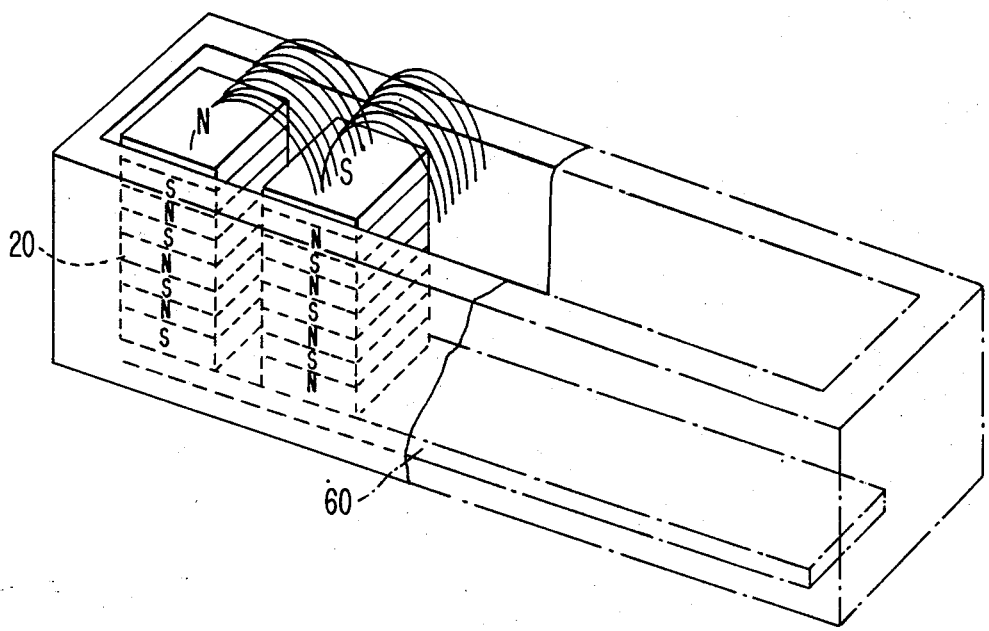
FIG. 3 depicts an arrangement or assembly of magnets in the system of the invention.

In FIG. 3, an array of magnets alternately oriented north to south and shunted at the bottom by "keeper" creates a magnetic field which covers the entire cross-section of the perfusion chamber (not shown), resting on the top of the array of magnets. By varying the number and/or orientation of magnets in each stack, the "throwing" power or depth of the magnetic field and intensity throughout the chamber can be altered.

Figure 4:
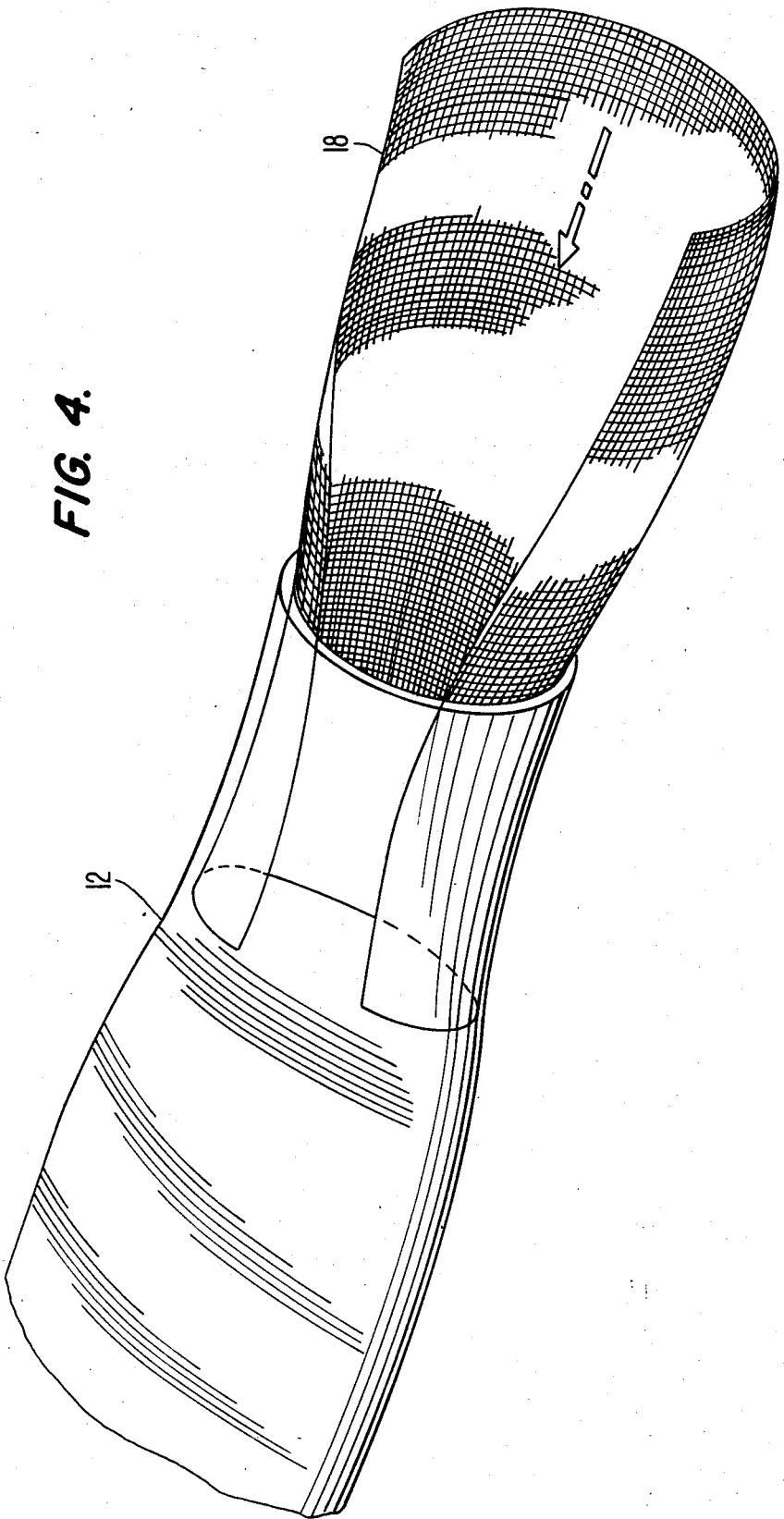
FIG. 4 depicts an arrangement of the mesh element and separation chamber of the system.

In FIG. 4, mesh element, preferably constructed of plastic monofilaments, is curled at the edges and positioned within chamber by insertion through either the inlet or outlet. After insertion, the mesh is retained in place by the natural recovery (memory) characteristics of the polymer.

The inlet 14 and outlet 16 means of the chamber 12 preferably comprise enlarged chambers compared to the cross-section of the separation zone to provide a space for capture of air bubbles. No transition angles to fluid flow greater than 45° should be present in the system to minimize bond disruption by eddy flows, etc.

The magnet assembly is preferably removable from beneath the perfusion chamber to facilitate stacking, removal, placement, orientation, etc. of the magnets in order to alter the magnetic field as desired. Non-magnetic spacer material is preferably provided between the stacks of magnets, to provide for low magnetic field spots in the chamber thereby cushioning the impact of magnetic particles with the wall of the chamber.

Soft iron keepers are preferably provided at the bottom of the magnet stack to preserve the magnetic field and act as shunting means where desired.

A further advantage of the present system is that it may be sterilized after assembly thereby avoiding the necessity for pre-sterilization and subsequent assembly of the sterilized components as is the case with the systems currently in use.

The magnetic particles are preferably microspheres constructed of any suitable material such as polystyrene. See Treleaven et al, supra, the disclosure of which is incorporated by reference herein. The microspheres are preferably formed with magnetic material, e.g., magnetite, contained therein.

I claim:

1. In a method for removing cells from bone marrow wherein said cells, bound to monoclonal antibodies, conjugated to magnetic particles, said method comprising flowing a liquid sample containing said bone marrow and magnetic conjugated antibodies bound to said cells through a zone provided with an inlet and an outlet associated with a magnetic field such that said liquid sample flowing there through and passes through said magnetic field whereby said bound cells and unconjugated particles are removed from said liquid sample by magnetic attraction, the improvement wherein:
    said magnetic field through which said liquid sample flows is non-uniform and is an ascending gradient from said inlet to said outlet.

2. The method of claim 1 wherein said particles are microspheres.

3. The method of claim 2 wherein said microspheres contain magnetite.

4. The method of claim 2 wherein said microspheres comprise polystyrene.

5. The method of claim 1 wherein said cells are malignant.

6. In a system for removing cells from bone marrow wherein said cells are bound by monoclonal antibodies, conjugated to magnetic particles, said system comprising (1) means defining a chamber provided with inlet and outlet means adapted to enable to flow through said chamber of a liquid sample containing said bone marrow and magnetic conjugated antibodies bound to said cells and (2) at least one magnetic field source associated with said chamber such that said liquid sample flowing therethrough passes through said magnetic field whereby said bound cells are removed from said liquid sample by magnetic attraction, the improvement wherein:
    said at least one magnetic field source comprises an assembly of plural magnets arranged such that said magnetic field is non-uniform and is an ascending gradient from said inlet means to said outlet means.
    said improvement further comprising means for eliminating movement in said chamber of said conjugated and any unconjugated magnetic particles after removal from said liquid sample.

7. The system of claim 6 wherein said movement elimination means is positioned so as to retard the flow of said conjugated and any unconjugated magnetic particles after capture thereof by said magnetic field.

8. The system of claim 7 wherein said movement elimination means comprises a mesh element adapted to prevent the escape of said conjugated and any unconjugated particles from said magnetic field.

9. The system of claim 8 wherein said mesh element is positioned adjacent the wall or walls of said chamber to which said conjugated or any unconjugated magnetic particles are attracted by said magnetic field.

* * * * *